(12) United States Patent
Leibinger et al.

(10) Patent No.: US 10,407,897 B2
(45) Date of Patent: Sep. 10, 2019

(54) MOBILE IMPLANT PRODUCTION UNIT

(71) Applicant: Karl Leibinger Medizintechnik GmbH & Co. KG, Mühlheim (DE)

(72) Inventors: Christian Leibinger, Mühlheim (DE); Michael Martin, Mühlheim (DE)

(73) Assignee: Karl Leibinger Medizintechnik GmbH & Co. KG, Mühlheim (DE)

(*) Notice: Subject to any disclaimer, the term of this patent is extended or adjusted under 35 U.S.C. 154(b) by 0 days.

(21) Appl. No.: 15/749,711

(22) PCT Filed: Jul. 18, 2016

(86) PCT No.: PCT/EP2016/067015
§ 371 (c)(1),
(2) Date: Feb. 1, 2018

(87) PCT Pub. No.: WO2017/021128
PCT Pub. Date: Feb. 9, 2017

(65) Prior Publication Data
US 2018/0230690 A1    Aug. 16, 2018

(30) Foreign Application Priority Data
Aug. 4, 2015    (DE) .................. 10 2015 112 774

(51) Int. Cl.
*E04B 1/348* (2006.01)
*E04H 3/08* (2006.01)
(Continued)

(52) U.S. Cl.
CPC ............ *E04B 1/3483* (2013.01); *A61G 3/001* (2013.01); *E04B 1/34336* (2013.01);
(Continued)

(58) Field of Classification Search
CPC ............ E04B 1/34869; E04B 1/34336; E04B 1/3483; A61G 3/001; E04H 3/08; E04H 5/02; E04H 1/125; E04H 2001/1283
(Continued)

(56) References Cited

U.S. PATENT DOCUMENTS 3,082,525 A    3/1963    Christensen
4,364,382 A    12/1982   Mennen
(Continued)

FOREIGN PATENT DOCUMENTS

DE    2161061 A1    3/1973
DE    3732128 A1    4/1989
(Continued)

OTHER PUBLICATIONS

Mar. 1, 2016—German Patent and Trademark Office Search Report of DE 102015112774.1.
(Continued)

*Primary Examiner* — Brian E Glessner
*Assistant Examiner* — Adam G Barlow
(74) *Attorney, Agent, or Firm* — Banner & Witcoff, Ltd.

(57) ABSTRACT

The invention relates to a medical container unit for designing and/or manufacturing an implant, comprising a plurality of container subunits, each of which forms a sector, is equipped with at least one means for designing and/or manufacturing an implant, and is formed by self-supporting partial substructures on at least two sides.

19 Claims, 1 Drawing Sheet

(51) Int. Cl.
*A61G 3/00* (2006.01)
*E04B 1/343* (2006.01)
*E04H 1/12* (2006.01)
*E04H 5/02* (2006.01)

(52) U.S. Cl.
CPC ........... *E04B 1/34869* (2013.01); *E04H 3/08* (2013.01); *E04H 1/125* (2013.01); *E04H 5/02* (2013.01); *E04H 2001/1283* (2013.01)

(58) Field of Classification Search
USPC .......................................................... 52/34
See application file for complete search history.

(56) References Cited

U.S. PATENT DOCUMENTS

| | | | |
|---|---|---|---|
| 4,741,698 A | 5/1988 | Andrews | |
| 5,052,930 A | 10/1991 | Lodde et al. | |
| 2008/0134589 A1* | 6/2008 | Abrams | E04B 1/003 52/79.1 |
| 2010/0139179 A1* | 6/2010 | Smith | E04B 1/34336 52/67 |
| 2011/0173898 A1 | 7/2011 | Denicourt et al. | |
| 2011/0173998 A1* | 7/2011 | Coleman | F25B 25/02 62/79 |
| 2014/0128923 A1 | 5/2014 | Ellis et al. | |
| 2014/0137493 A1* | 5/2014 | Mouzannar | E04H 3/08 52/234 |
| 2014/0207197 A1 | 7/2014 | Reisberg | |
| 2014/0248583 A1 | 9/2014 | Rostami | |
| 2015/0152634 A1* | 6/2015 | Unger | E04B 1/3483 52/79.2 |
| 2015/0209093 A1 | 7/2015 | Dallis | |
| 2016/0160515 A1* | 6/2016 | Wallance | E04B 1/3483 52/79.1 |

FOREIGN PATENT DOCUMENTS

| | | |
|---|---|---|
| DE | 9104004 U1 | 6/1991 |
| DE | 29616357 U1 | 11/1996 |
| DE | 299 09 616 U1 | 11/1999 |
| DE | 10 2008 051 532 A1 | 4/2010 |
| DE | 10 2008 058 035 A1 | 5/2010 |
| DE | 202012002433 U1 | 3/2012 |
| DE | 202012003175 U1 | 5/2012 |
| DE | 10 2013 102 178 A1 | 7/2014 |
| EP | 1748126 A1 | 1/2007 |
| FR | 2541714 A1 | 8/1984 |
| FR | 2631813 A1 | 12/1989 |
| GB | 770696 A | 3/1957 |
| WO | 02/39921 A1 | 5/2002 |
| WO | 2008/027234 A2 | 3/2008 |
| WO | 2011/136775 A1 | 11/2011 |
| WO | 2014/188036 A1 | 11/2014 |
| WO | 2015057722 A1 | 4/2015 |
| WO | 2015/155296 A1 | 10/2015 |

OTHER PUBLICATIONS

Sep. 28, 2016—International Search Report of PCT/EP2016/067015 (with English translation).
Sep. 28, 2016—Written Opinion of International Search Report of PCT/EP2016/067015 (German).
Jul. 4, 2016 (DE) German Office Action—App No. 102015112774.1.
Mar. 29, 2017 (EP) European International Search Report—App No. PCT/EP2016/079244.
Jul. 25, 2016 (DE) German Office Acton—App No. 10 2015 122 793.2.
May 15, 2019—(CN) Office Action—App 201680044635.9—Eng Tran.

* cited by examiner

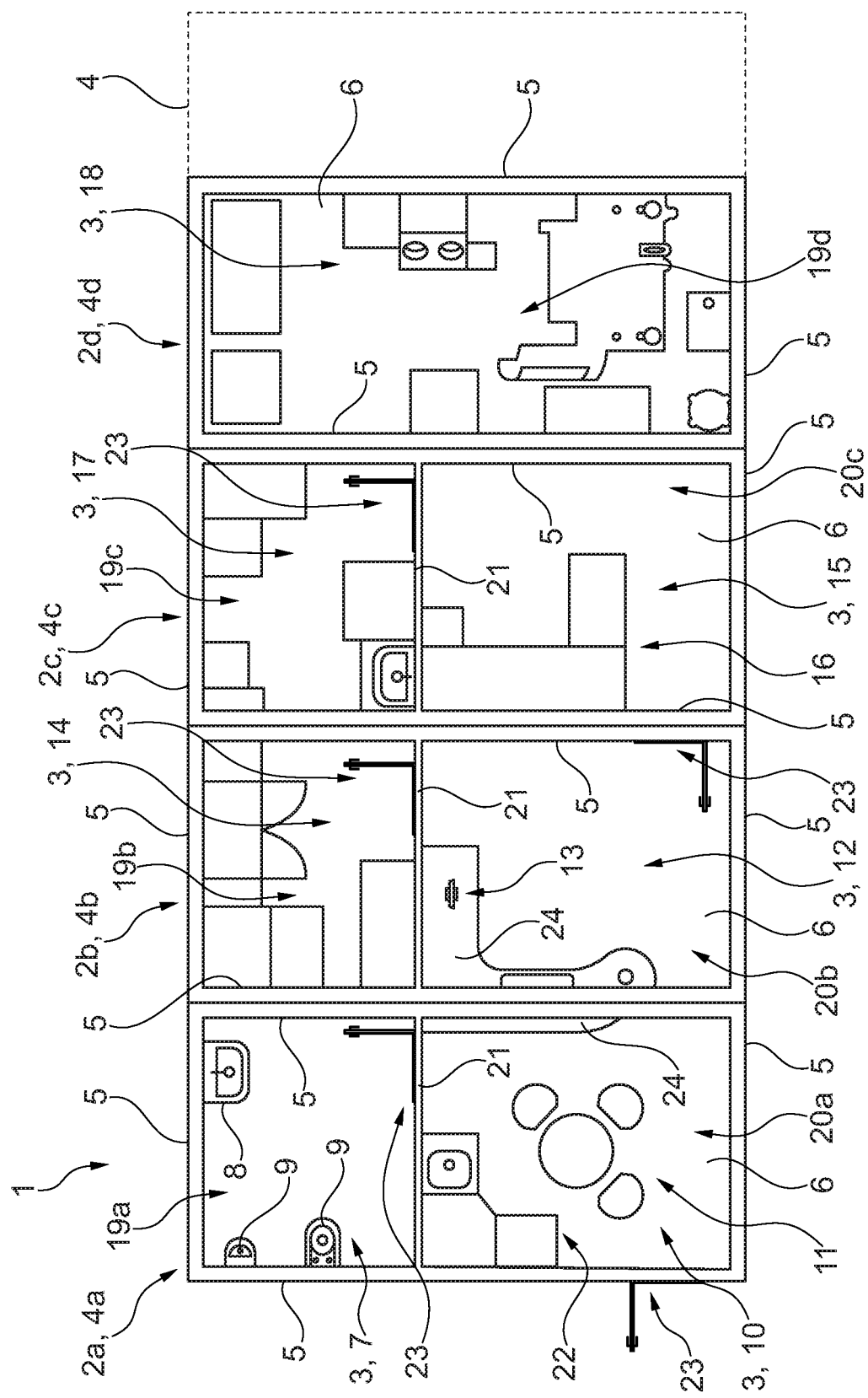

MOBILE IMPLANT PRODUCTION UNIT

CROSS-REFERENCE TO RELATED APPLICATIONS

This application is a U.S. National Stage application under 35 U.S.C. § 371 of International Application PCT/EP2016/067015, published as WO 2017/021128, filed Jul. 18, 2016, which claims priority to German Patent Application DE 102015112774.1, filed Aug. 4, 2015, each of which are hereby incorporated by reference in their entireties.

The invention relates to a medical container unit (i.e. a mobile container device) for designing and/or manufacturing an implant for a patient which has a plurality of sectors.

It is already known from the generic state of the art to basically provide containers for medical purposes. For example, US 2011/0173898 A1 in this context discloses an independent medical care unit.

Further state of the art is known from DE 20 2012 003 175 U1, wherein a modular space can be structured in skeleton design, for example an operating room in the medical sector, with plural support profiles being used for forming a ceiling skeleton.

In the medical containers known from prior art it has turned out to be a drawback, however, that they, each per se, pursue a particular application, with the sectors thereof constituting fixed required components of the respective container. In particular, said containers can be used only in the completely assembled state of the container in respective interaction so as to realize the intended function of the container. Therefore, it has not been possible so far to react to the respective spatial situation at the mounting location of the container and to make available an overall container unit which can be individually adapted to the conditions there. Therefore, so far containers individually adapted to the respective spatial situation at the mounting location have had to be produced.

Therefore, it is the object of the present invention to eliminate said drawbacks known from prior art and, especially, to provide a medical container unit which is intended to be individually adapted to the respective desired spatial conditions in the application area, with the manufacture of said container being intended to be kept especially inexpensive.

In accordance with the invention, this is achieved by the features of claim 1, wherein the container unit is equipped with plural container subunits each forming a sector and wherein each container subunit is equipped with at least one means for designing and/or manufacturing a (preferably patient-specific) implant and is configured/delimited by self-supporting partial substructures on at least two sides. In this way, each of the sectors is configured/formed by individually/independently self-supporting container (space) subunits. Also, sectors are provided in this way which are arranged in the form of the container subunits adapted to be positioned independently of each other/separated from each other.

This arrangement enables medical container units of different height, width and length in response to the basic dimensions of the container subunits to be constructed. In this way, a container/container unit can be designed in an especially versatile manner.

For treating and healing the patient it is of advantage when patient-specific, anatomically adapted implants are provided as quickly as possible and thus the period between patient admission and operation can be minimized. Moreover, it is of advantage when for an advance check of the operating technique models of the implants can be quickly made available to the surgeon. By integrating all designing and/or manufacturing steps in a transportable container unit transport times are omitted. Moreover, direct and immediate communication between attending the physician and the technician dealing with the designing and/or manufacturing unit is possible.

Further advantageous embodiments are claimed in the subclaims and shall be illustrated hereinafter.

When advantageously each container subunit is detachably connected to at least one further container subunit, the container/container unit is designed to be especially robust in the mounted state, but at the same time the individualized adaptation of the outer geometry can be quickly carried out.

It is further also useful when each container subunit includes a self-supporting skeletal structure at which plural partial substructures are present to which plate sections forming plural side walls, a ceiling and/or a bottom (preferably in the form of panels) and/or beams supporting the former are arranged/fastened. This ensures that each container subunit is even more stable per se/in detail and its individual sector can be mounted/produced independently of the other sectors. This offers especially advantages for transporting the container/the container unit by disassembly into the individual sectors which then can be placed on the respective transport vehicle in an especially space-saving manner.

When the skeletal structure is made, in this context, from a metallic material, preferably a steel material, the skeletal structure may be designed to be especially compact while still being adapted to absorb the required bearing load. Preferably, the skeletal structure is constructed by plural interconnected supporting beams or is expanded by further supporting beams/beams. This allows to form the container subunits per se to be equally especially thin-walled.

When, in this context, the plate sections are made from a light-metal material, preferably aluminum material, or especially preferred from plastic material, the lining/wall of the container/container unit is also configured in an especially simple and inexpensive manner.

It is further advantageous when one of the sectors/a first sector/one of the container subunits/a first container subunit is equipped with a sanitary unit comprising a lavatory, a shower and/or a toilet bowl, and/or comprising an office unit including office furniture. Preferably, said (first) sector is configured to include both the sanitary unit and the office unit, with the latter being spatially delimited against each other by means of a (preferably re-detachable) inner wall. This allows for especially efficient use of a sector.

In this context, it is also further advantageous when one of the sectors/a second sector/one of the container subunits/a second container subunit is equipped with an (implant) designing unit comprising a computer including a drawing software (i.e. a CAD program) and/or with a cleaning and/or packaging unit for the implant. Preferably said (second) sector is configured to comprise both the designing unit and the cleaning and/or packaging unit, the latter then being spatially delimited against each other by a (preferably detachable) inner wall. This allows to make especially efficient use of a second sector, too.

When furthermore one of the sectors/a third sector/one of the container subunits/a third container subunit is equipped with a handcraft unit comprising a workbench and/or with a surface finishing unit for the implant, also such sector is configured to be especially useful. The handcraft unit and the surface finishing unit in turn are preferably arranged in said (third) sector and are separated from each other by a further (preferably re-detachable) inner wall.

It is further useful when one of the sectors/a fourth sector/one of the container subunits/a fourth container subunit is equipped with a manufacturing unit for machine fabrication of the implant comprising an additive manufacturing device/machine, a sintering device/machine, a laser fusing device/machine and/or a cutting device/machine such as a milling device/machine. This allows to make especially efficient use of a fourth sector, too. In addition, the benefit of the container is further improved as patient-specific implants can be made available to the surgeon on site/in the hospital as quickly as possible.

It is further advantageous when the container subunits can be stacked individually or further preferred in pairs/can be stacked on top of each other (re-detachably) or can be (re-detachably) stringed together. Especially preferred, the container subunits are configured, however, such that they can be (re-detachably) connected/stringed both next to each other/horizontally and stacked on top of each other/vertically/(re-detachably) connected to each other. This allows to realize especially versatile container designs.

Further, it is of advantage when each container subunit is configured/prepared for receiving at least one inner wall, preferably plural re-detachable inner walls.

Also, the invention relates to a method of designing and/or manufacturing an implant comprising individual (designing and/or manufacturing) steps which are carried out e.g. exclusively inside a hospital and a container unit affiliated thereto according to any one of the afore-described designs.

In other words, according to the invention a mobile implant production container unit which provides a production device for manufacturing implants and can be individually adapted to the given spatial options at the place of use is thus realized. Said container/container unit then is preferably mounted during its assembly as a structure on a vehicle and/or stationarily when mounted at a particular location. Thus, patient-specific implants can be fabricated and can be made available as quickly as possible without any long supply and dispatch channels. The production device/container unit may be mounted at a central location (for example in urban centers) or else inside a hospital. The implants are designed based on CT data (patient scan) by a software designing tool made available to the surgeon and are transferred to the local production device. There the implant is machine-manufactured and handed over to the surgeon.

Consequently, the medical container can be assembled either as a fixed container in the form of an office container or as a structure onto a service vehicle of a service company. In this way, the patient-specific implants are made available to the surgeon as quickly as possible. The production of implants is ensured by qualified and validated processes in mobile units/the container unit, wherein manufacture can be carried out as quickly as possible and can be facilitated especially worldwide at all distribution sites. Therefore, the advantages include the fact that the manufacture can be both stationary and mobile, the manufacture can be composed in modular design (one technology for each container/container subunit) and thus can be ideally scaled/expanded to the needs. Depending on the required technology, the corresponding container unit including the individually necessary sectors/container subunits is made available. The container unit thus can be scaled especially properly.

The individual sections/container subunits of the container unit can be scaled relative to each other as well as when considered absolutely so as to take the needs for including differently large groups of persons such as physicians and engineers/technicians, as well as differently large and frequent manufacturing batches into account.

The container unit is provided, dimensioned and configured for being operated in direct vicinity of the operating wing of a hospital. Advantageously, it may also be directly connected to the building parts of the operating wing of the hospital.

Hereinafter, the invention shall be illustrated in detail by way of a FIGURE in which a schematic bird's eye top view onto a medical container unit according to the invention in accordance with a preferred embodiment is shown from which the individual sectors/container subunits of the container unit as well as an exemplary arrangement of the same are evident.

The FIGURE is merely schematic and serves exclusively for the comprehension of the invention.

FIG. 1 illustrates an advantageous embodiment of a medical container unit 1 according to the invention. The medical container unit 1 in this embodiment serves as a mobile designing and manufacturing space unit for an implant of a patient. Said mobile container unit 1 is in the form of an independent single container and can be transported by means of a transport vehicle. It can be mounted on a mounting surface, such as a mounting surface inside a hospital. In another configuration, the container unit 1 is connected to a transport vehicle as a vehicle structure which is also re-detachable. The container unit 1 forms a structure of a service vehicle.

The container unit 1 of the type according to the invention, also referred to as container or overall container unit, includes plural independent, i.e. individually self-supporting container subunits 4a to 4d having partial substructures. Each container subunit 4a to 4d forms a sector 2a to 2d. In this configuration, more than two, viz. four sectors 2a to 2d are formed by respective container subunits 4a to 4d, the container subunits 4a to 4d jointly forming the container unit 1 in their connected state. In further configurations, also more than four (indicated by the broken line), such as 5 or 6, or less than four, such as two or three, of the container subunits 4a to 4d are interconnected, however, to form the container unit 1 without deviating from the basic inventive idea.

In this embodiment, the four independent container subunits 4a to 4d are juxtaposed in series and are re-detachably fastened/re-detachably connected to each other. The container subunits 4a to 4d have an equal/identical design with respect to a skeletal structure of their four sidewalls 5 schematically illustrated here and to a ceiling not shown in detail here for the sake of clarity as well as with respect to their bottom 6. Each of the container subunits 4a to 4d thus forms a type of module connected by fastening to at least one further container subunit 4a to 4d to form the container unit 1. Each container subunit 4a to 4d includes the skeletal structure as supporting structure especially for supporting/bearing the four sidewalls 5 and the ceiling, which skeletal structure at least partially forms the partial substructure. Said skeletal structure is formed by means of plural supporting beams in the form of steel beams forming the supporting structure of the individual container subunits 4a to 4d. This helps to accommodate/support the four sidewalls 5 and the ceiling by part of the integrated skeletal structure and also to configure each of the container subunits 4a to 4d to be individually self-supporting. Then in turn plural plate-shaped sections/plate sections are connected to the skeletal structure so as to delimit the sector 2a to 2d toward the environment and to ensure formation of the four sidewalls 5, of the bottom 6 and of the ceiling.

The bottom 6 of the respective sector 2a to 2d/of the respective container subunit 4a to 4d is provided/shaped of a flat plate section which here is configured as a sole bottom plate defining the basic dimensions of each of the container subunits 4a to 4d. The bottom plate/the bottom 6 is rectangular in this case. The bottom plate is made from massive metallic material, preferably from a steel material. The ceiling, too, is formed/shaped by means of such plate section or alternatively by plural plate sections, the latter then being connected to the skeletal structure. Each sidewall 5, too, is shaped in the usual way by means of plural plate sections attached to line the skeletal structure. Especially, each container subunit 4a to 4d is completely lined with plate sections on a side facing the environment/facing away from the neighboring container subunit 4a to 4d so that its respective sector 2a to 2d is delimited against the environment. The plate sections thus in total form an area/space separated from the environment in the connected state of the container subunits 4a to 4d forming the container unit 1. The skeletal structure and the plate sections of a container subunit 4a to 4d are arranged so that they are re-detachable/removable in areas adjacent to a neighboring container subunit 4a to 4d. This enables the individual sectors 2a to 2d to be spatially interconnected.

While the skeletal structure is made from a steel material/plural interconnected steel supports/beams and, resp., is connected by beams, the plate sections are preferably made from aluminum material, alternatively also from plastic material.

In addition, the detailed structure of the individual sectors 2a to 2d is evident from FIG. 1. A first sector 2a/a first container subunit 4a includes a sanitary unit 7 (as a first means 3) inside a first subspace 19a. Said sanitary unit 7 forms sort of a bathroom and includes both a lavatory 8 and plural toilet bowls 9. A second subspace 20a of the first sector 2a is arranged in turn to be spatially separated from the first subspace 19a via a removable/re-detachable inner wall 21. In this configuration, the second subspace 20a of the first sector 2a is an office. Consequently, the second subspace 20a includes an office unit 10 (as a second means 3) comprising office furniture 11 as well as kitchen furniture 22. In the inner wall 21 between the first subspace 19a and the second subspace 20a a door 23 is arranged through which the staff members may change between the subspaces 19a and 20a. The sidewall 5 of the first sector 2a/the first container subunit 4a arranged on a side facing away from a second sector 2b and forming an outer wall also includes a door 23 in the form of an external door.

The longitudinal side of a second container subunit 4b is flush with the longitudinal side of the first container subunit 4a. The second sector 2b formed by the second container subunit 4b in turn includes two subspaces 19b and 20b, the first subspace 19b having a cleaning and packaging unit 14 (as a third means 3). At least one cleaning device is present for cleaning a finished implant, for example a spray cleaner or a compressed air cleaner, and a packaging device for packaging the afore-cleaned implant is present for further transport to a patient/a surgeon. It is also imaginable to dispose only either a cleaning unit or a packaging unit in said first subspace 19b. A second subspace 20b of the second sector 2b in turn includes a designing unit 12 (as a fourth means 3). Said designing unit 12 in turn includes an electronic computer 13 of which merely a monitor/image display device is shown from above for the sake of clarity. By means of said computer 13 which is connected to further computers/databases also via an external data communication such as Internet, patient-specific 3D data detected before of a patient/a body area to be treated of the patient are transmitted/received. Thus, the computer 13 includes a receiving unit by means of which 3D data sets of the respective patient can be processed. The computer 13 also includes drawing software, i.e. a CAD program, by which an implant is produced by way of the transmitted geometric 3D data of the patient.

The two subspaces 19b and 20b of the second sector 2b are equally spatially separated from each other by means of a removable/re-detachable inner wall 21 in which also a door 23 is inserted. In this configuration, the sidewalls 5 between the second subspace 20a of the first sector 2a and the second subspace 20b of the second sector 2b are free from plate sections and thus are spatially interconnected, as is evident from the desk 24 of the designing unit 12 extending from the subspace 20b into the subspace 20a.

A third container subunit 4c in turn is arranged to be re-detachable with a longitudinal side to a longitudinal side of the second container subunit 4b facing away from the first container subunit 4a. Also, the third sector 2c formed by the third container subunit 4c is split and has a first subspace 19c and a second subspace 20c. The first subspace 19c in turn includes a surface finishing unit 17 (as a fifth means 3) by means of which a surface of the implant prefabricated before can be finished. The first subspace 19c of the third sector 2c is delimited against the second subspace 20c by means of a removable/re-detachable inner wall 21 and a door 23. In the second subspace 20c a handcraft unit 15 is arranged (as a sixth means 3) which inter alia includes a workbench for performing possible finishing on the implant fabricated before. The first subspace 20c of the third sector 2c is connected to the second subspace 20b of the second sector 2b via another door 23, the adjacent sidewalls 5 of the two container subunits 4b and 4c being spared in the area of said door 23.

On a longitudinal side of the third container subunit 4c facing away from the first and second container subunits 4a and 4b in turn a fourth container subunit 4d is arranged with its longitudinal side and is re-detachably attached to the third container subunit 4c. A fourth sector 2d formed by said fourth container subunit 4d is configured as a single space 19d and includes plural manufacturing devices of an implant constituting a manufacturing unit 18 (as a seventh means 3). Here especially the arrangement of preferably an additive manufacturing device such as a 3D printer, further preferred of a sintering device, further preferred of a laser fusing device, especially preferred of a cutting device such as a milling device in the manufacturing unit 18 is realized. By means of the manufacturing unit 18 and, resp., the corresponding manufacturing device, especially a medical/surgical implant can be manufactured. After manufacturing/producing the implant within said fourth sector 2d, the implant can be fed to the handcraft unit 15, the surface finishing unit 17 and the cleaning and packaging unit 14.

Apart from said four sectors 2a to 2d, any number of further sectors can be composed to form the overall container unit 1 by further container subunits 4 which in turn are re-detachably connectable to the container subunits 4a to 4d, which is schematically represented by the broken lines on the side of the fourth container subunit 4d in FIG. 1.

Each container subunit 4a to 4d also has an equal surface area predefined by the bottom 6/the bottom plate. All sectors 2a to 2d have a rectangular/square flat surface area/bottom area. Especially preferred, said bottom area is from 40% to 60% in width, further preferred half its length, about 3 m by 6 m. In height each of the container subunits 4a to 4d is preferably smaller than 4 m so that they can also be mounted in a normally configured room of a hospital. By way of example, the height of each of said container subunits 4a to 4d/sectors 2a to 2d is between 2.50 and 3.50, especially preferred about 3 m/3 m. When arranging two container subunits 4a to 4d juxtaposed in pairs, such as the first container subunit 4c and the second container subunit 4b or the third container subunit 4c and the fourth container subunit 4d, an approximately square surface area of the assembly of two container subunits 4a to 4d is resulting.

In this way, a method of designing and manufacturing the implant for a patient/a surgical treatment comprising individual designing and manufacturing steps carried out e.g. exclusively inside the hospital and the container unit 1 affiliated thereto is realized in an especially efficient manner. The manufacturing steps are realized exclusively inside the container. The design may be carried out partly or completely outside the container.

Alternatively to the positioning of the container subunit 4a to 4d arranged in series to form the container unit 1 according to FIG. 1, it is also possible to stack the same partially such as in pairs or all of them on top of each other. The individual sectors 2a to 2d therefore are configured so that they cannot only be connected/stringed next/horizontally to each other, but they can be stacked/connected to each other on top of each other/vertically as well. In vertical stacking the adjacent ceilings and bottoms of two container subunits 4a to 4d are connected by a staircase. When stacking two container subunits 4a to 4d, such as the third and fourth container subunits 4c and 4d, in pairs onto two other container subunits 4a to 4d, such as the first and second container subunits 4a and 4b, an overall cubical-shaped container unit 1 is formed. The container subunits 4a to 4d are always (re-detachably) connected to their neighboring container subunits 4a to 4d.

LIST OF REFERENCE NUMERALS 1 container unit
2a first sector
2b second sector
2c third sector
2d fourth sector
3 designing and/or manufacturing means
4a first container subunit
4b second container subunit
4c third container subunit
4d fourth container subunit
5 sidewall
6 bottom
7 sanitary unit
8 lavatory
9 toilet bowl
10 office unit
11 office furniture
12 designing unit
13 computer
14 cleaning and packaging unit
15 handcraft unit
16 workbench
17 surface finishing unit
18 manufacturing unit
19a first subspace of the first sector
19b first subspace of the second sector
19c first subspace of the third sector
19d space of the fourth sector
20a second subspace of the first sector
20b second subspace of the second sector
20c second subspace of the third sector
21 inner wall
22 kitchen furniture
23 door
24 desk

The invention claimed is:

1. A medical container unit for designing and/or manufacturing a patient-specific, anatomical adapted implant, the container unit comprising a plurality of container subunits each of which forms a sector and is formed by self-carrying partial substructures on at least two sides, wherein one sector includes an implant designing unit comprising a computer with a drawing software for designing the patient-specific, anatomical adapted implant, and the one sector or another sector includes an implant machine-manufacturing unit adapted to machine fabricate the patient-specific, anatomical adapted implant.

2. The container unit according to claim 1, wherein each container subunit is re-detachably connected to at least one further container subunit.

3. The container unit according to claim 1, wherein each container subunit includes a self-supporting skeletal structure at which a plurality of partial substructures is present at which plate sections forming plural sidewalls, a ceiling and/or a bottom and/or beams supporting the same are arranged.

4. The container unit according to claim 3, wherein the skeletal structure is composed of a metallic material.

5. The container unit according to claim 3, wherein the plate sections are composed of a light-metal material or a plastic material.

6. The container unit according to claim 1, wherein a first sector is equipped with a sanitary unit comprising a lavatory, a shower and/or a toilet bowl and/or with an office unit comprising office furniture.

7. The container unit according to claim 1, wherein a first sector is equipped with a cleaning and/or packaging unit and/or a sterilization unit.

8. The container unit according to claim 1, wherein a first sector is equipped with a handcraft unit comprising a workbench and/or with a surface finishing unit.

9. The container unit according to claim 1, wherein the implant machine-manufacturing unit for machine fabricating the patient-specific, anatomical adapted implant comprises an additive manufacturing device, a sintering device, a laser fusing device and/or a cutting device.

10. The container unit according to claim 1, wherein a first container subunit and a second container subunit of the plurality of container subunits are stacked on top of each other.

11. The container unit according to claim 1, wherein the another sector includes the implant machine-manufacturing unit for machine fabricating the patient-specific, anatomical adapted implant, wherein the one sector and the another sector are separated by an inner wall.

12. The container unit of claim 11, wherein the inner wall is re-detachable.

13. The container unit of claim 11, wherein the inner wall comprises a door.

14. The container unit of claim 1, wherein the plurality of container subunits comprises at least two container subunits having a different height.

15. The container unit of claim 1, wherein the plurality of container subunits comprises at least two container subunits having a different width.

16. The container unit of claim 1, wherein the plurality of container subunits comprises at least two container subunits having a different length.

17. The container unit of claim 1, wherein the one sector and the another sector have different two-dimensional areas.

18. The container unit of claim 1, wherein the one sector and the another sector have different three-dimensional areas.

19. The container unit of claim 1, wherein one container unit of the plurality of container subunits comprises two sectors.

* * * * *